(12) United States Patent
Xu et al.

(10) Patent No.: US 9,778,249 B2
(45) Date of Patent: Oct. 3, 2017

(54) SEQUENCE AND CHIRAL SELECTIVITY OF DNA-DRUG INTERACTIONS REVEALED BY FORCE SPECTROSCOPY

(71) Applicant: UNIVERSITY OF HOUSTON SYSTEM, Houston, TX (US)

(72) Inventors: Shoujun Xu, Houston, TX (US); Qiongzheng Hu, Houston, TX (US); Yuhong Wang, Houston, TX (US); Te-Wei Tsai, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 15/514,683

(22) PCT Filed: Sep. 25, 2015

(86) PCT No.: PCT/US2015/052355
§ 371 (c)(1),
(2) Date: Mar. 27, 2017

(87) PCT Pub. No.: WO2016/049526
PCT Pub. Date: Mar. 31, 2016

(65) Prior Publication Data
US 2017/0234860 A1    Aug. 17, 2017

Related U.S. Application Data

(60) Provisional application No. 62/055,897, filed on Sep. 26, 2014.

(51) Int. Cl.
G01N 33/553 (2006.01)
C12Q 1/68 (2006.01)
G01N 33/53 (2006.01)

(52) U.S. Cl.
CPC ....... *G01N 33/5308* (2013.01); *C12Q 1/6804* (2013.01); *G01N 2500/04* (2013.01); *G01N 2500/20* (2013.01)

(58) Field of Classification Search
None
See application file for complete search history.

(56) References Cited

U.S. PATENT DOCUMENTS

| | | | |
|---|---|---|---|
| 7,060,448 B2 * | 6/2006 | Henderson | C07K 16/065 356/501 |
| 2004/0067544 A1 * | 4/2004 | Vogel | C07K 16/1232 435/7.32 |
| 2009/0325259 A1 * | 12/2009 | Vogel | C07K 14/245 435/174 |
| 2012/0020892 A1 * | 1/2012 | Xu | A61K 49/1872 424/9.34 |

OTHER PUBLICATIONS

De Silva et al., "Well-defined and sequence-specfici noncovalent binding forces of DNA", The Journal of Physical Chemistry B, vol. 117, No. 25, 2013, 7554-7558.*

(Continued)

*Primary Examiner* — Chris L Chin
(74) *Attorney, Agent, or Firm* — Conley Rose, P.C.

(57) ABSTRACT

Methods of quantifying the efficiency of a drug molecule for its targeted receptor, using a differential binding force to quantify the efficiency of a drug molecule to its targeted receptor.

20 Claims, 8 Drawing Sheets

(56) References Cited

OTHER PUBLICATIONS

Doughty et al, "Binding of the anti-cancer drug daunomycin to DNA probed by second harmonic generation", The Journal of Physical Chemistry B, vol. 117, No. 49, 2013, 15285-15289.*
Qu et al, "Allosteric, Chiral-selective drug binding to DNA", PNAS, vol. 97, No. 22, 2000, 12032-12037.*
Yao et al, "Force-induced remnant magnetization spectroscopy for specific magnetic imaging of molecules", Angewandte Chemie International Edition, vol. 123, No. 19, 2011, 4499-4501.*
Hu et al, "Sequence and chiral selectivity of drug-DNA interactions revealed by force spectroscopy", Angewandte Chemie International Edition, vol. 53, No. 51, 2014, 14135-14138.*

\* cited by examiner

SEQUENCE LISTING

<160> NUMBER OF SEQ ID NOS: 5

<210> SEQ ID NO 1
<211> LENGTH: 12
<212> TYPE: DNA
<213> ORGANISM: ARTIFICIAL
<220> FEATURE:
<223> OTHER INFORMATION: Artificial DNA sequence used to deterimine
      molecular binding force

<400> SEQUENCE: 1
cccgggtttc cc                                                          12

<210> SEQ ID NO 2
<211> LENGTH: 12
<212> TYPE: DNA
<213> ORGANISM: ARTIFICIAL
<220> FEATURE:

```
<223> OTHER INFORMATION: Artificial DNA sequence used to deterimine
      molecular binding force

<400> SEQUENCE: 2
gggcccaatg gg                                                        12

<210> SEQ ID NO 3
<211> LENGTH: 12
<212> TYPE: DNA
<213> ORGANISM: ARTIFICIAL
<220> FEATURE:
<223> OTHER INFORMATION: DNA sequence to test molecular binding force.

<400> SEQUENCE: 3
cccaatcgac cc                                                        12

<210> SEQ ID NO 4
<211> LENGTH: 12
<212> TYPE: DNA
<213> ORGANISM: ARTIFICIAL
<220> FEATURE:
<223> OTHER INFORMATION: DNA SEQUENCE TO TEST MOLECULAR BINDING FORCE.

<400> SEQUENCE: 4
gggtcgattg gg                                                        12

<210> SEQ ID NO 5
<211> LENGTH: 13
<212> TYPE: DNA
<213> ORGANISM: ARTIFICIAL
<220> FEATURE:
<223> OTHER INFORMATION: DNA SEQUENCE FOR TESTING MOLECULAR BINDING
      FORCE

<400> SEQUENCE: 5
cgcgaaaaac gcg                                                       13
```

SEQUENCE AND CHIRAL SELECTIVITY OF DNA-DRUG INTERACTIONS REVEALED BY FORCE SPECTROSCOPY

CROSS-REFERENCE TO RELATED APPLICATIONS

The present application is the U.S. National Stage under 35 U.S.C. §371 of International Patent Application No. PCT/US2015/052355, filed Sep. 25, 2015, which claims priority to U.S. Provisional Application No. 62/055,897 filed Sep. 26, 2014, the disclosures of which are herein incorporated in their entirety by reference.

STATEMENT REGARDING FEDERALLY SPONSORED RESEARCH OR DEVELOPMENT

This invention was made with government support under Grants No. ECCS-1028328 and ECCS-1508845 both of which were awarded by the United States National Science Foundation. The United States government has certain rights in the invention.

BACKGROUND

Field of the Disclosure

This disclosure generally relates to methods of quantifying the efficiency of a drug molecule for its targeted receptor. More particularly, this disclosure is drawn to methods of using a differential binding force to quantify the efficiency of a drug molecule to its targeted receptor. Further, this disclosure relates to a method of quantifying: enantiomeric selectivity of drugs for a target; the selectivity of a series of drugs for a target; and the selectivity of a DNA sequence for binding to a receptor/target or ligand.

Background of the Technology

The interactions between small molecules, such as ions and drug molecules, and nucleic acids are widely encountered in biological functions and drug development. Among the most important aspects in characterizing these systems are the sequence selectivity of the DNA and the conformational selectivity of the drug molecules. Various techniques have been applied to study drug-DNA systems, including nuclear magnetic resonance (NMR), second harmonic generation, fluorescence, circular dichroism UV melting,[9] X-ray,[10] atomic force microscopy (AFM),[11,12] and optical tweezers. However, none of these techniques can adequately, and directly measure the binding strength of such interactions with a sufficiently high force resolution, so that different DNA-drug interactions can be distinguished. Therefore, a method to quantify the efficiency of a drug molecule to its targeted receptor; a method of quantitatively measuring DNA sequence selectivity to a ligand or a receptor; and the enantiomeric selectivity of a molecule for its receptor/target would be well received in the field.

BRIEF SUMMARY OF THE DISCLOSED EMBODIMENTS

In order to address such needs, the disclosure provides in some embodiments described herein: a method of quantifying the efficiency of a drug molecule to a receptor by measuring a differential binding force. The method comprises: (a) conjugating a magnetic particle to a ligand to form a magnetic particle-ligand conjugate; (b) adding said conjugate to a receptor, wherein said receptor is immobilized on a surface, and forming a ligand-receptor complex; (c) measuring a first magnetization of said complex; (d) subjecting said complex to a gradually increasing force, wherein said force is increased in increments, and measuring the magnetization at each incremental force value; (e) measuring the dissociation force (F1) of the complex, (f) reforming the complex; (g) adding a drug molecule to said complex to form a second complex; or alternatively, adding the drug molecule to the receptor prior to step f, then adding the ligand to form the second complex; (h) measuring the dissociation force (F2) of said second complex by repeating steps d and e; and (i) subtracting F1 from F2 to quantify the differential binding force of said drug molecule to said ligand-receptor complex. In some embodiments of the method, in step e, said dissociation of the complex occurs when consecutive magnetization values decrease by a maximum value (wherein the absolute slope of the magnetization-force curve reaches a maximum value). In some embodiments the force range may be 0.1 to about 900 pN. In some other embodiments of the method of quantifying the efficiency of a drug molecule to a receptor by measuring a differential binding force the ligand is selected from a group comprising nucleic acids and proteins, in other embodiments the receptor is selected from a group comprising nucleic acids and proteins. In further embodiments, the drug molecule is selected from the group comprising synthetic organic molecules and molecules extracted from natural products, and in still further embodiments the drug molecule is label-free. In other embodiments of the method of quantifying the efficiency of a drug molecule to a receptor by measuring a differential binding force, the drug molecule is a racemic mixture, in further embodiments the drug molecule is an enantiomer.

In another embodiment a method of determining enantiomeric selectivity of a drug for a target is disclosed; the method comprises: (a) conjugating a magnetic particle to a ligand to form a magnetic particle-ligand conjugate; (b) adding said conjugate to a receptor, wherein said receptor is immobilized on a surface, and forming a ligand-receptor complex; (c) measuring a first magnetization of said complex; (d) subjecting said complex to a gradually increasing force, wherein said force is increased in increments, and measuring the magnetization at each incremental force value (wherein the force increment depends on the mass of the magnetic particles and the centrifugal speed, and comprises a range in some embodiments of 0.1-10 pN, and in further embodiments 1-5 pN); (e) measuring the dissociation force (F1) of the complex, (f) reforming the complex; (g) adding a first enantiomer to said complex to form a second complex; or alternatively, adding the first enantiomer to the receptor prior to step f, then adding the ligand to form the second complex; (h) measuring the dissociation force (F2) of said second complex by repeating steps d and e; (i) subtracting F1 from F2 to quantify the differential binding force of said first enantiomer to said ligand-receptor complex; (j) adding a second enantiomer to said complex to form a second-enantiomer complex comprising the second enantiomer; or alternatively, adding the second enantiomer to the receptor prior to step f, then adding the ligand to form the second-enantiomer complex comprising the second enantiomer; (k) measuring the dissociation force (F2') of said second-enantiomer complex comprising the second enantiomer by repeating steps d and e; (l) subtracting F1 from F2' to quantify the differential binding force of said second enantiomer to said ligand-receptor complex; (m) subtracting said differential binding force of said second enantiomer from said differential binding force of said first enantiomer; and determining which enantiomer is most tightly bound to said receptor. In further embodiments of the method, at step (e), and step (c) the dissociation of the complex occurs when consecutive magnetization values decrease by a maximum value. In another embodiment, of the method of determining enantiomeric selectivity of a drug for a target, the ligand is selected from a group comprising nucleic acids and proteins, in another embodiment the receptor is selected from a group comprising nucleic acids and proteins, in a further embodiment the drug molecule is selected from the group comprising synthetic organic molecules and molecules extracted from natural products, and in a still further embodiment the drug molecule is label-free.

In another embodiment, a method of determining the selectivity of a nucleic acid sequence for a drug molecule is disclosed; the method comprises: (a) conjugating a magnetic particle to a ligand to form a magnetic particle-ligand conjugate; (b) adding said conjugate to a first receptor wherein said first receptor comprises a first nucleic acid sequence, and wherein said first receptor is immobilized on a surface and forming a ligand-first-receptor complex; (c) measuring a first magnetization of said ligand-first-receptor complex; (d) subjecting said ligand-first-receptor complex to a gradually increasing force, wherein said force is increased in increments, and measuring the magnetization at each incremental force value; (e) measuring the dissociation force (F1) of the ligand-first-receptor complex, (f) reforming the ligand-first-receptor complex; (g) adding a drug molecule to said complex to form a second ligand-first-receptor complex; or alternatively, adding the drug molecule to the receptor prior to step f, then adding the ligand to form the second ligand-first-receptor complex; (h) measuring the dissociation force (F2) of said second complex by repeating steps d and e; (i) subtracting F1 from F2 to quantify the differential binding force of said drug molecule to said ligand-first-receptor complex; (j) adding said conjugate to a second receptor, wherein said second receptor comprises a second nucleic acid sequence that differs from said first receptor by at least one nucleic acid, and wherein said receptor is immobilized on a surface and forming a ligand-second-receptor complex; (k) measuring a first magnetization of said ligand-second-receptor complex; (l) subjecting said ligand-second-receptor complex to a gradually increasing force, wherein said force is increased in increments, and measuring the magnetization at each incremental force value; (m) measuring the dissociation force (F1') of the ligand-second-receptor complex, (n) reforming the ligand-second-receptor complex; (o) adding a drug molecule to said ligand-second-receptor complex to form a second ligand-second-receptor complex; or alternatively, adding the drug molecule to the receptor prior to step (f), then adding the ligand to form the second ligand-second-receptor complex; (p) measuring the dissociation force (F2') of said second ligand-second-receptor complex by repeating steps d and e; (q) subtracting F1' from F2' to quantify the differential binding force of said drug molecule to said ligand-second-receptor complex; (r) comparing said differential binding force of said drug molecule to said ligand-second-receptor complex and the differential binding force of said drug molecule to said ligand-first-receptor complex; and (s) determining from step r the selectivity of said nucleic acid sequence of said receptors for said drug molecule. In another embodiment, wherein in step (e), and step (c) the dissociation of the complex occurs when consecutive magnetization values decrease by a maximum value. In a further embodiment, the ligand is selected from a group comprising nucleic acids and proteins, in a still further embodiment, said first and second receptors are selected from a group comprising nucleic acids and proteins; in another embodiment the drug molecule is selected from the group comprising synthetic organic molecules and molecules extracted from natural products; and in a further embodiment the drug molecule is label-free.

DETAILED DESCRIPTION OF THE DISCLOSED EMBODIMENTS

It should be understood at that although an illustrative implementation of one or more embodiments are provided below, the disclosed systems and/or methods may be implemented using any number of techniques, whether currently known or in existence. The disclosure should in no way be limited to the illustrative implementations, drawings, and techniques below, including the exemplary designs and implementations illustrated and described herein, but may be modified within the scope of the appended claims along with their full scope of equivalents.

The following discussion is directed to various exemplary embodiments of the invention. However, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and that the scope of this disclosure, including the claims, is not limited to that embodiment.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct engagement between the two devices, or through an indirect connection via other intermediate devices and connections. As used herein, the term "about," when used in conjunction with a percentage or other numerical amount, means plus or minus 10% of that percentage or other numerical amount. For example, the term "about 80%," would encompass 80% plus or minus 8%.

Force-induced remnant magnetization spectroscopy (FIRMS) technique uses external mechanical forces to distinguish noncovelant bonds including DNA binding. The force resolution has been shown to reached 1.8 pN, and is sufficient to resolve DNA duplexes with one basepair difference (see for example U.S. Pat. No. 8,802,057 incorporated herein in its entirety by reference).[16]

The external force may include shaking force, centrifugal force, or an acoustic radiation force. The FIRMS technique is based on the fact that dissociated magnetic particles that label biological molecules have no net magnetic signal because of their randomized magnetic dipoles. Therefore, as each bond dissociates and the magnetic particle is no longer bound it is effectively measured because there is a decrease in the overall magnetic signal.

Herein, embodiments of a method to quantify the efficiency (of binding) of a drug molecule to its targeted receptor are disclosed. Further a method of quantitatively measuring a DNA sequences' selectivity to a ligand or a target/receptor is also disclosed; further, a method of quantifying the enantiomeric selectivity of a molecule for its receptor/target is disclosed, thereby using differential binding force to precisely characterize the mechanical effect of a molecular species binding to a target. Therefore, the high-resolution binding forces measured by the FIRMS technique disclosed herein distinguishes the binding mode/behavior among drug molecules of different chirality; DNA of various sequences; and drug molecules of differing target selectivity, all of which are critical in drug design and mechanistic studies.

EXAMPLES

Figure 1:
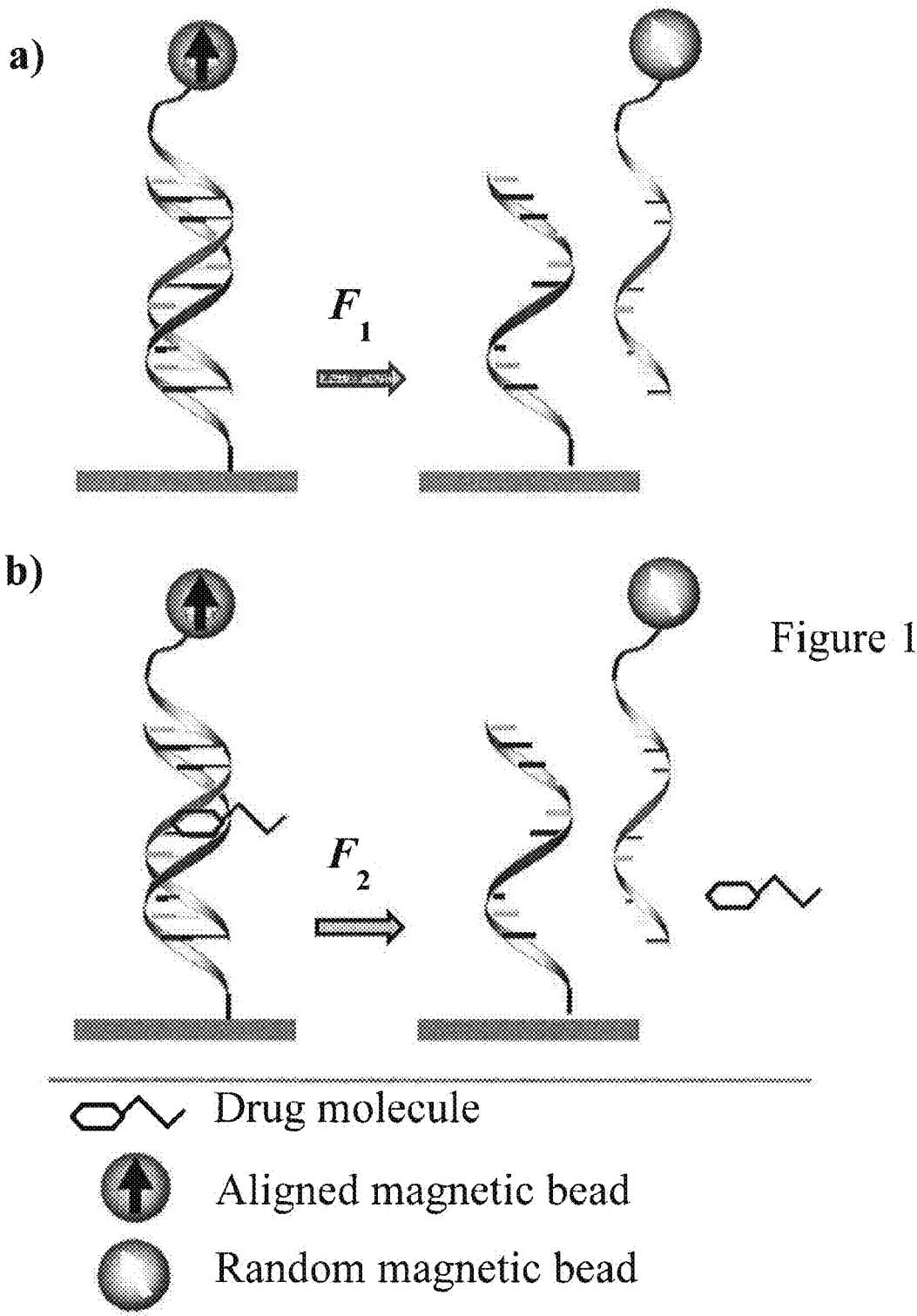
FIG. 1: depicts a schematic of an embodiment of a method described herein: wherein one strand of the DNA duplex is immobilized on a surface, while the other is labeled with a magnetic particle. The binding forces of the DNA duplex are measured in the absence and presence of the drug molecule, denoted as $F_1$ and $F_2$, respectively. The differential binding force, $F_2-F_1$, characterizes the influence of the drug-DNA binding on the stability of the DNA (the binding forces are obtained as described herein)

Some embodiments of the method of using a differential binding force to quantify the efficiency of a drug molecule to a receptor comprises a process wherein one strand of the DNA duplex is immobilized on a surface, while the other is labeled with a magnetic particle. The binding forces of the DNA duplex are measured in the absence and presence of the drug molecule, denoted as $F_1$ and $F_2$, respectively. The differential binding force, $F_2-F_1$, characterizes the influence of the drug-DNA binding on the stability of the DNA. The binding forces are obtained using the FIRMS technique, depicted in FIG. 1.

Example 1

Characterizing DNA Sequence Specificity for a Ligand

Figure 2:
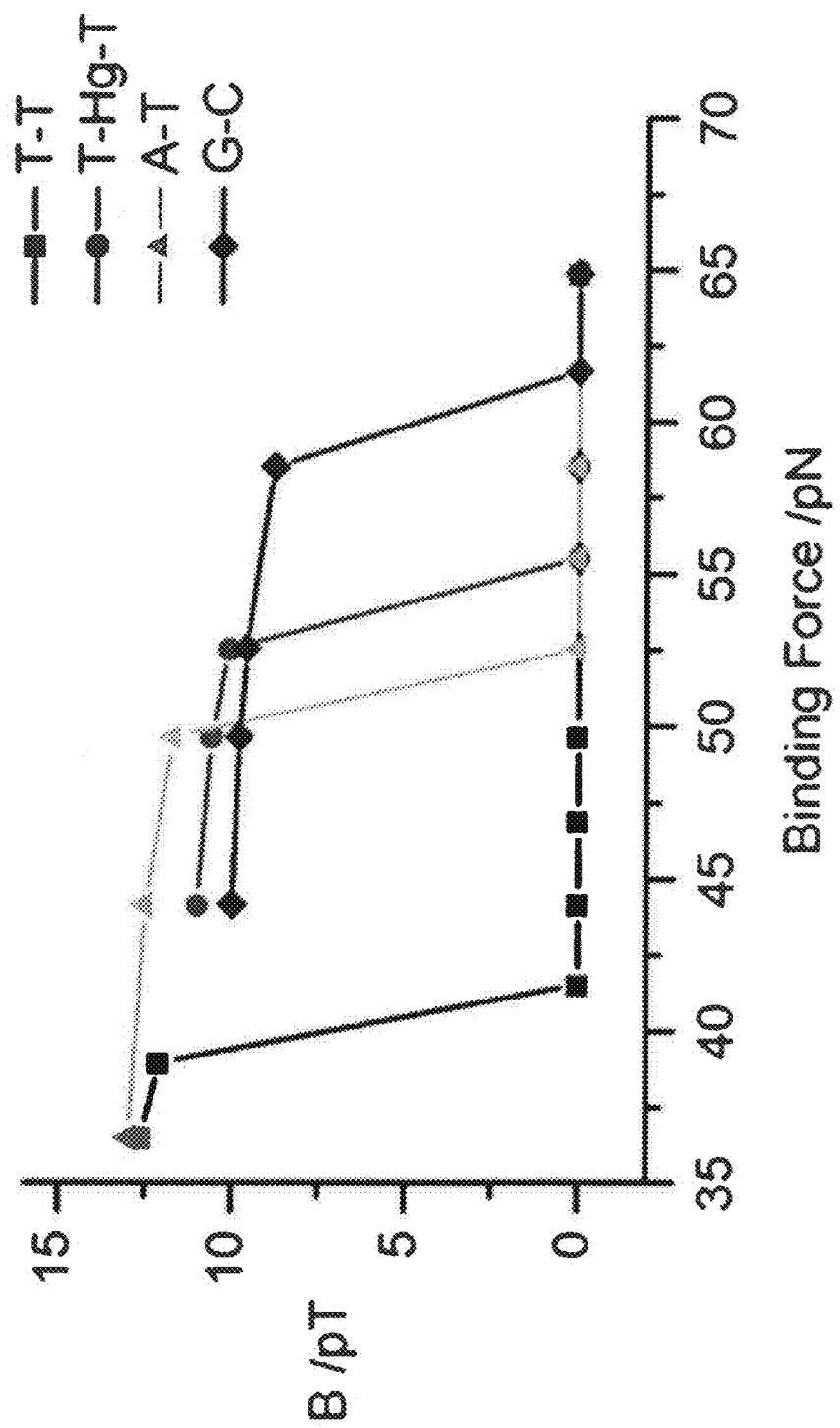
FIG. 2: graphically depicts the measurements of the T-Hg-T binding force and shows the comparison with the differential binding forces of T-Hg-T with A-T and C-G pairs.

An embodiment of the method herein described is used to quantify the binding modes of the T-Hg-T system (T, thymine), in which Hg refers to $Hg^{2+}$. This system has been studied by NMR as well as other spectroscopic techniques. It is therefore known that Hg specifically intercalates into a DNA duplex at the T-T mismatching pair. Based on the previous results, the binding of T-Hg-T is weaker than that of C-G but stronger than A-T. FIG. 2 graphically depicts the measurements of the T-Hg-T binding force and comparison with the differential binding forces of A-T and C-G pairs, as measured by the method described herein and depicted in FIG. 1.

Experimental Details:

Magnetic particles M280 were used to label one strand of the DNA duplexes as previously characterized. After initial magnetization by a permanent magnet, the magnetic signal of the particles were detected by an atomic magnetometer, with a sensitivity of 200 $fT/(Hz)^{1/2}$. Sample wells (4×2×1 $mm^3$) with a biotin-coated bottom surface were used to immobilize the other strand of the DNA duplexes. Mechanical forces were applied using a centrifuge (Eppendorf 5417R).

The sample well, with dimensions of 4×2×1 $mm^3$ (L×W×D), was coated with biotin on the bottom surface. An aqueous solution of 0.625 mg/mL streptavidin was loaded into the sample well and incubated for 1 hr. Then the sample well was rinsed three times with a buffer solution as described below. 8 □L of 10 □M biotinylated target DNA strand was transferred onto the streptavidin-decorated surface and incubated for 1 hr. After rinsing the surface, 8 □L of 10 □M biotinylated probing DNA strand was in contact with the target DNA-modified surface overnight. The formed DNA duplex was rinsed with buffer solution. Subsequently, 8 □L of 1% bovine serum album (BSA) was introduced into the sample well and incubated for 1 hr before the addition of the streptavidin-coated magnetic particles (Invitrogen, M280). The particles were pre-washed three times with the buffer solution. After incubation for 2 hrs, the physically absorbed magnetic particles were removed from the surface by applying centrifuge with the speed of 1000 rpm for 5 min. The sample was then magnetized for 2 min using a permanent magnet (~0.5 T). Further, the intercalators of interest, including $Hg^{2+}$, daunomycin, and d- and l-THP, were introduced into the surface-immobilized magnetic particles immersed under the buffer solution and kept for 1 hr. Forces with varying amplitudes were applied on the samples by gradually increasing the speed of the centrifuge. The centrifuge time for each speed was 5 min.

Magnetization measurements were performed using scanning magnetic imaging with an atomic magnetometer with a sensitivity of about 200 $fT/\sqrt{Hz}$. For the T-Hg-T system, 10 mM HEPES (N-2-hydroxyethylpiperazine-N'-2-ethanesulfonic acid) buffer (pH=7.6) containing 0.5 M $NaNO_3$ and 0.05% Tween-20 was used. The intercalation of daunomycin into DNA duplexes was performed using the TE buffer (50 mM Tris, 138 mM NaCl, 2.7 mM KCl, 1 mM EDTA, and 0.05% Tween-20, pH=8.0). The interactions between THP and DNA duplexes were investigated with BPES buffer (6 mM $Na_2HPO_4$, 2 mM $NaH_2PO_4$, 185 mM NaCl, 1 mM EDTA, and 0.05% Tween-20, pH=7.0).

Figure 7:
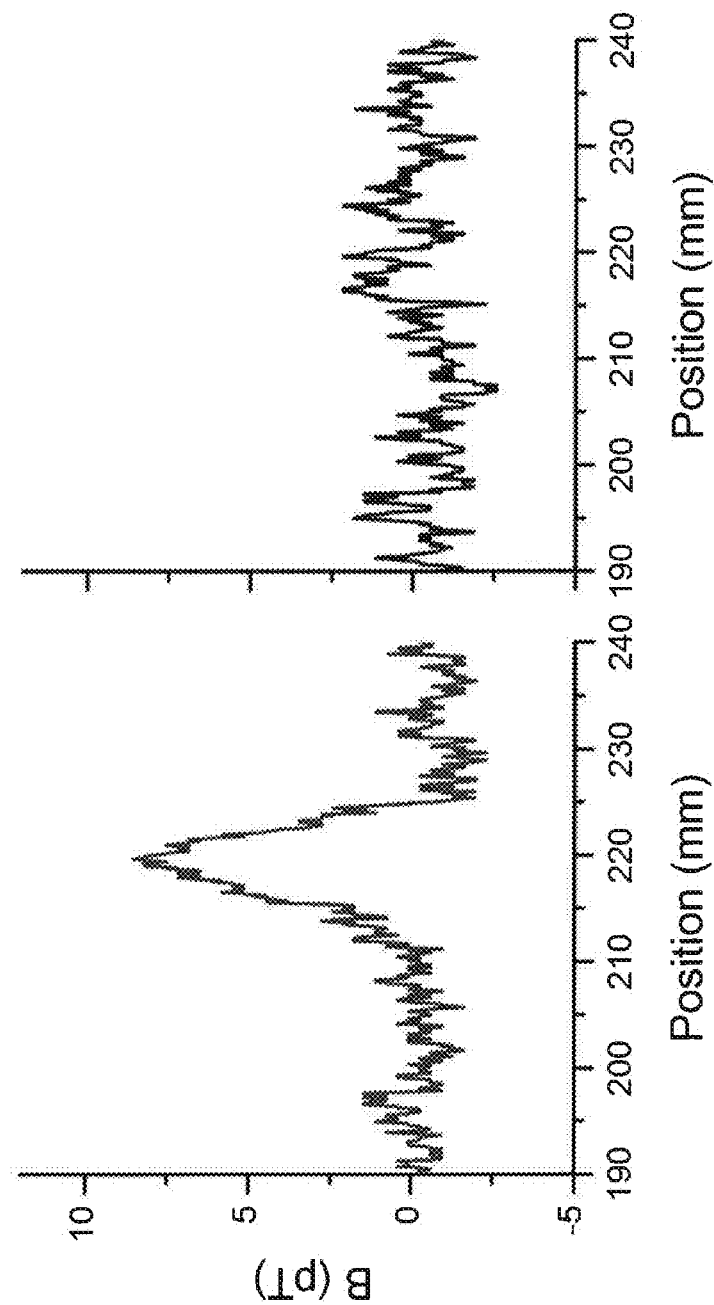
FIG. 7: depicts a graph showing the magnetic signals (a) red (left plot), before bond dissociation, and (b) blue (right plot), after bond dissociation.

Magnetic signals before and after bond dissociation: The magnetic particles in the sample well were magnetized only once by a permanent magnet, wherein a decrease in the remnant magnetic signal represents the dissociation of the noncovalent bonds (*J. Phys. Chem. B* 117, 7554-7558 (2013). The magnetic detection was obtained using a scanning magnetic imaging method (*Angew. Chem. Int. Ed.* 48, 5679-5682 (2009)). FIG. 7, thus shows the embodiments of magnetic field profiles before and after the dissociation of the DNA duplex with an additional C-G pairing in the T-Hg-T experiments. The results correspond to the data points at 58 and 61 pN on the blue trace in FIG. 2 (far right trace).

The sudden decrease in the magnetic signal from 3800 rpm to 3900 rpm indicates the dissociation of the DNA duplex. Given the buoyant mass of the particles being $4.6 \times 10^{-15}$ kg and the radius of the centrifuge of 8 cm, the binding forces were calculated by the method herein described (and depicted in FIG. 1) to be to be 58 and 62 pN respectively, according to the equation:  (*J. Phys. Chem. B* 117, 7554-7558 (2013)).

Therefore, the force resolution calculated by an embodiment of the method herein described is approximately 2 pN. The DNA sequence used for Hg binding was:

5'-CCC GGG TT<u>T</u> CCC-3'
3'-GGG CCC AA<u>T</u> GGG-5', which contains a T-T pair as underlined (SEQ. 1 and SEQ. 2 respectively). The binding force of the DNA duplex was determined to be 40 pN, calculated from the buoyant mass of the magnetic particles, the centrifugal speed at which the dissociation occurred, and the radius of the centrifuge.

Upon binding with Hg, the binding force increased to 54 pN, representing a 14 pN increase. For comparison, the T-T pair was replaced in the duplex with A-T and C-G respectively. Their binding forces were measured to be 51 and 60 pN, respectively. The differential binding forces are thereby 11 pN for A-T and 20 pN for C-G, in this particular DNA platform. The results are consistent with AFM results, which gave 9±3 pN for A-T binding and 20±3 pN for C-G pairing. Typical magnetic signals before and after DNA duplex dissociation are depicted in FIG. 7. Comparing the differential binding forces as calculated herein, leads to the following binding order: A-T<T-Hg-T<C-G, and is consistent with the order of melting points in the literature. Therefore, the results validate the application of FIRMS measurement of differential binding forces for characterizing the binding between small molecules and DNA duplexes. (Qiongzheng Hu, and Shoujun Xu, *Sequence and Chiral Selectivity of DNA-Drug Interactions Revealed by Force Spectroscopy, Angewandte Chemie International Edition*, Vol. 53, 51, pg 14135-14138, Dec. 15, 2014).

Example 2

Elucidation and Quantification of Sequence Selectivity

Figure 8:
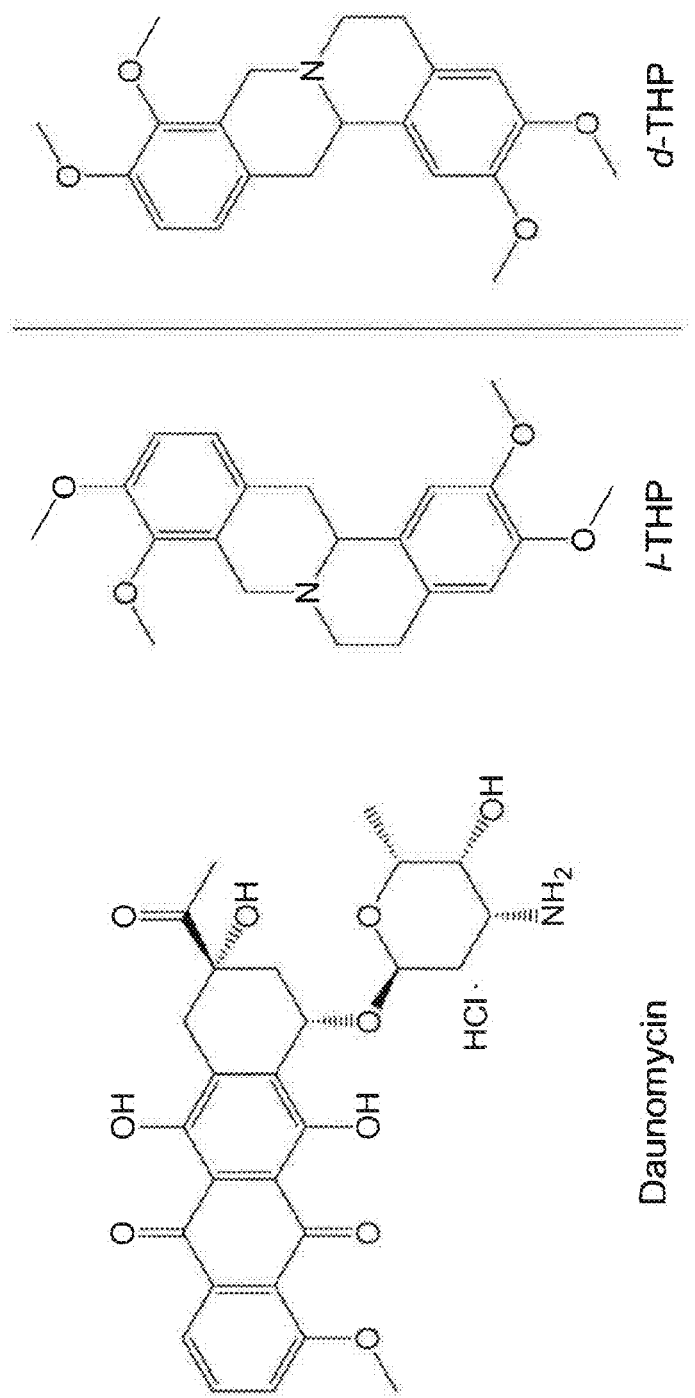
FIG. 8: depicts the molecular structures of daunomycin and d, l-THP.

Two DNA molecules were herein tested for their binding selectivity by the methods herein disclosed (chemical structures are shown in FIG. 8). The drug molecule tested was daunomycin, a commonly used anticancer drug, which preferentially binds to specific triplex sequences in DNA duplexes.

DNA Intercalation is widely considered as its binding mode, although minor groove binding has also been discussed, however, the specificity has previously not been quantified by binding strength. In order to measure the binding forces of daunomycin into different DNA duplexes, the target DNA strand used was 5'-CCC AAT <u>CGA</u> CCC-3' (SEQ. 3), wherein the probe DNA was a 12 bp complementary DNA strand, 5'-GGG <u>TCG</u> ATT GGG-3' (SEQ. 4). The duplex is represented as $DNA_1$. Based on the previous reports, daunomycin may have specifically bound to the CGA segment. As a control experiment the differential binding force of daunomycin with a different DNA duplex, $DNA_2$, with sequence 5'-CCC GGG TTT CCC-3' and its complementary strand was measured. $DNA_2$, however does not contain a CGA segment.

Figure 3:
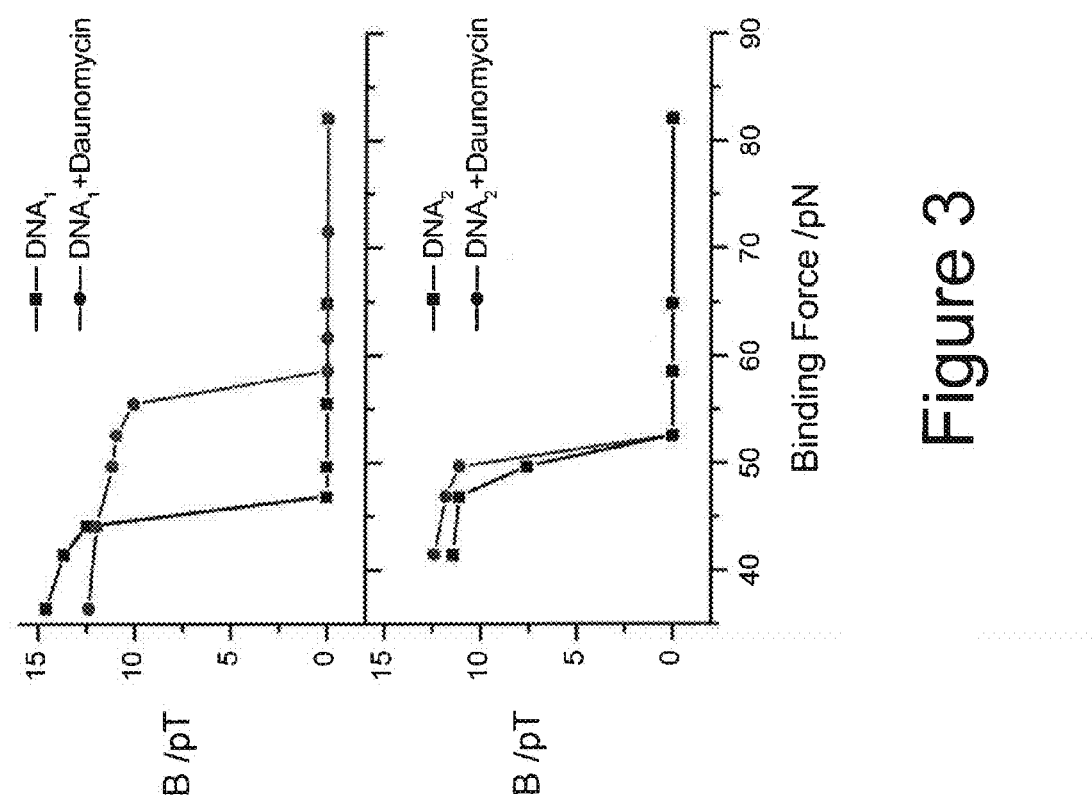
FIG. 3: depicts DNA sequence specificity (as measured by an embodiment of the method herein) for daunomycin binding. a) shows specific binding of daunomycin with a DNA duplex, $DNA_1$. b) shows nonbinding between daunomycin with a second DNA, $DNA_2$.

The results of the binding experiments are shown in FIG. 3. Upon intercalating with daunomycin, the binding force of $DNA_1$ increased from 45 pN to 57 pN. In contrast, no significant force difference was observed in the control experiment with $DNA_2$: the binding force was 51 pN for the DNA and 52 pN for $DNA_2$-daunomycin complex. The results are consistent with the literature in that daunomycin specifically target the CGA sequence. The differential binding force of 12 pN shows that the contribution of daunomycin intercalation to the thermal stability is similar to that of the A-T pairing, but substantially smaller than that of C-G pairing. Thus the drug molecule is specific for $DNA_1$ as clearly measured by the differential binding energy of 12 pN.

Example Three

Elucidation & Quantification of Enantomeric Selectivity

In a further embodiment the method herein described was applied to another drug molecule: tetrahydropalmatine (THP). THP is a natural alkaloid racemate extracted from Rhizoma Corydalis. Racemic d/l THP is included in the active compounds that result in the antitumor effect of Corydalis.

Although it has been reported that racemic THP shows enantioselective binding to DNA using gas chromatography, the features for the d-THP and l-THP were largely unresolved. In addition, the investigation on interactions between THP and DNA duplex is rare. It remained previously unknown whether the binding force of the DNA duplex could be increased after incubation of the alkaloid with DNA duplexes, which is valuable for understanding the antitumor activity of the drug molecule.

Figure 4:
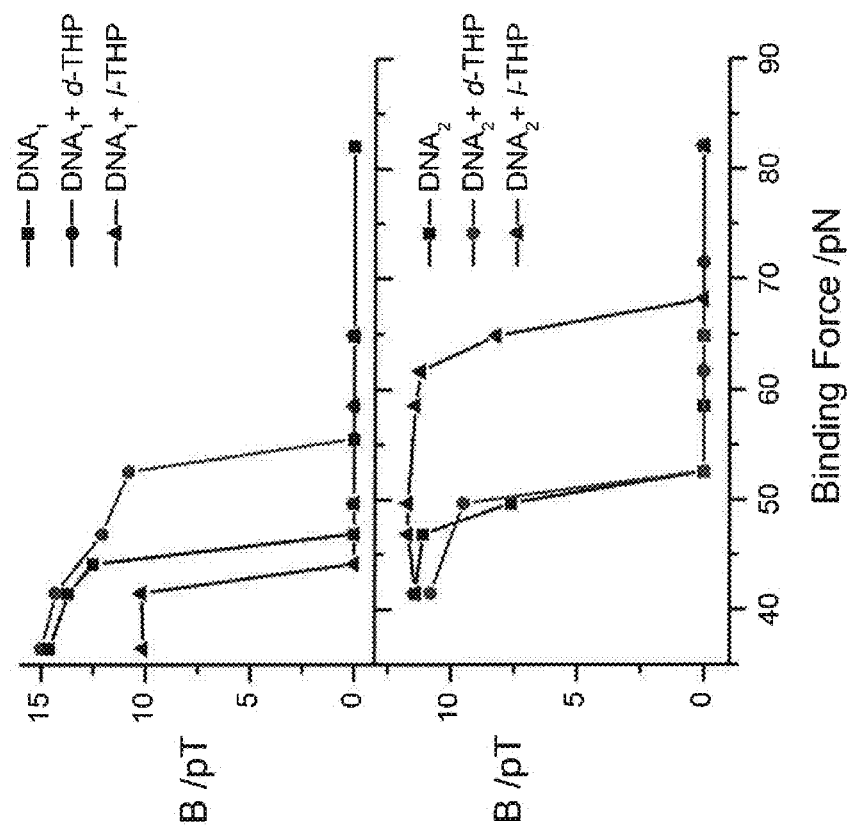
FIG. 4: depicts sequence specificity and chiral selectivity of DNA intercalating with tetrahydropalmatine (THP), wherein a) $DNA_1$ selectively binds with d-THP; and b) $DNA_2$ selectively binds with l-THP.

The binding of THP with the two DNA sequences used in the previous daunomycin experiment was performed. Both d- and l-THP were studied with each DNA sequence. The results are shown in FIG. 4. For $DNA_1$ (FIG. 4*a*), the binding of l-THP led to the binding force of the duplex increasing from 44 pN to 54 pN, producing a differential binding force of 10 pN. This value shows that effective binding took place between $DNA_1$ and d-THP, with a binding strength similar to the A-T pairing. Conversely, $DNA_1$ incubated with l-THP did not yield a binding force increase. The complex had a binding force of 43 pN, thus no significant binding occurred between $DNA_1$ and l-THP.

The behaviors of both chiral molecules bound with $DNA_2$ were however in opposite fashion. In FIG. 4*b*, the binding force of $DNA_2$-d-THP complex was 51 pN, which is essentially the same as that of the DNA alone. However, $DNA_2$-l-THP complex increased the binding force to 66 pN. The differential binding force of 15 pN is in between the binding of A-T and C-G pairing.

Figure 5:
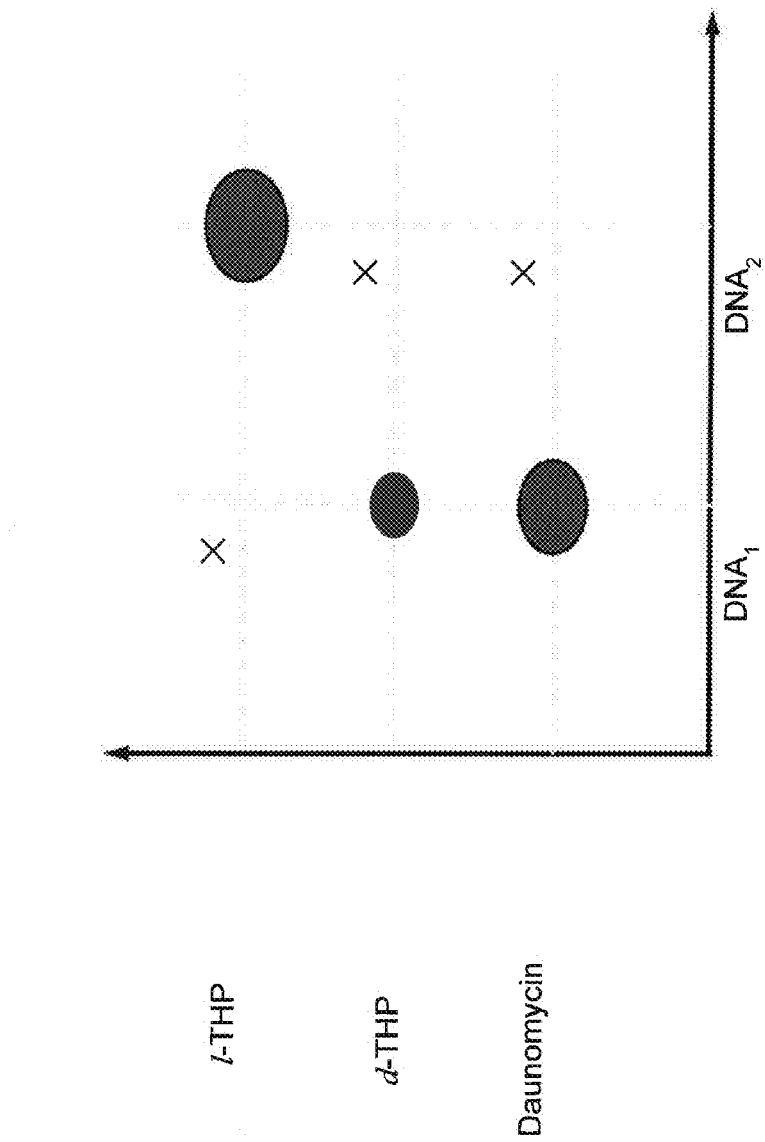
FIG. 5: depicts a mapping of differential binding forces for two DNA sequences with intercalating drug molecules, daunomycin and (d, l)-THP. Wherein a cross signifies zero differential binding force; and a circle signifies positive differential binding force, with circular area indicating the relative amplitude.

The differential binding forces of the various drug-DNA systems described herein, and measured by embodiments of the method of measuring the differential binding forces are further summarized in FIG. 5. This map clearly shows the mutual selectivity between DNA and drug molecules. For instance, $DNA_1$ binds with both daunomycin and d-THP, with the former being slightly stronger than the latter, whereas it does not significantly bind with l-THP. In some complicated cases, it may be common to have many similar drug structures and multiple potential DNA targets, such a map of differential binding force will therefore provide a clear way of representing binding selectivities. The high-resolution FIRMS method described herein therefore accurately determines the differential binding force and therefore the enantomeric and sequence selectivities of a drug molecule interacting a nucleotide sequence.

Example Four

Quantification of Groove Binding Between DNA and Drugs

Figure 6:
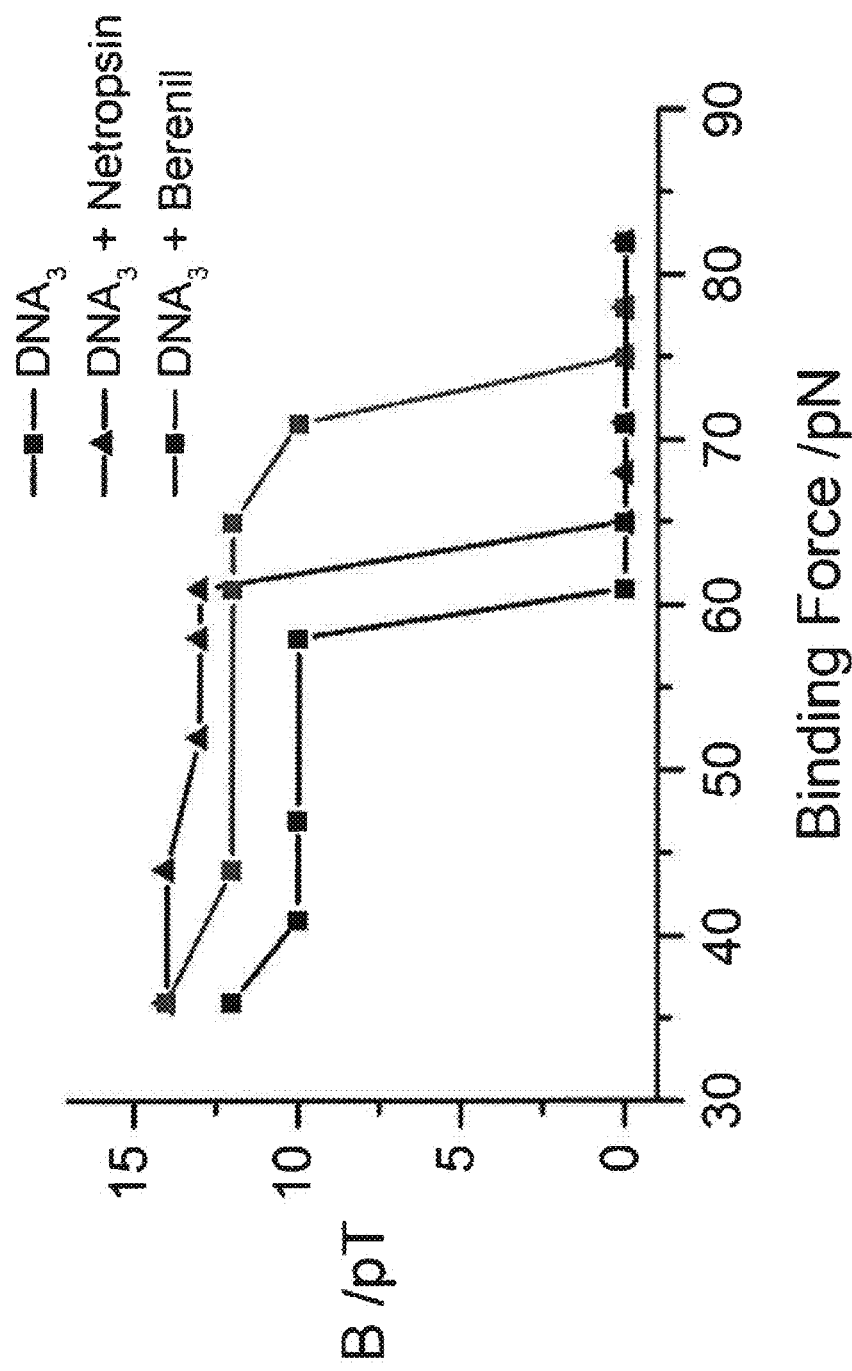
FIG. 6: depicts the differential binding forces of two groove-binding drugs, netropsin and berenil. Their binding mode is different from the intercalation interaction of daunomycin and THP.

The method of differential binding force can also be used to quantify a different binding mode of DNA-drug interactions. We chose two groove-binding drugs, netropsin and berenil. The groove-binding interaction is different from the intercalation interaction of daunomycin and THP. Shown in FIG. 6 are the binding forces of DNA alone, DNA with netropsin, and DNA with berenil, with values of 59, 63, and 73 pN, respectively. The DNA sequence was 5'-CGC-GAAAAACGCG-3' (SEQ. 5). The binding forces yield differential binding force of 4 pN for netropsin and 14 pN for berenil. The results clearly show that berenil binds stronger to the target DNA duplex.

The method of using differential binding force is not limited to drug-DNA systems. It may be of equal value in general ligand-receptor systems involving drug molecules. The binding of the drug molecule will alter the effectiveness of the ligand-receptor recognition. Furthermore, the differential binding force does not have to be positive; a negative value will indicate reduced binding specificity between the ligand and receptor molecules. Possible examples may be inhibitors, which are designed to block the receptors from their corresponding ligands. Drug resistance studies may also be probed, where single point mutations in nucleotides will result in changes of binding forces for a probe molecule, or SAR may be probed for a series of drugs and a target in a high throughput fashion.

Therefore, embodiments of the method herein provided measure differential binding forces by using high-resolution FIRMS, and may be utilized in (but not limited to) drug screening and other applications involving noncovalent molecular binding. A further benefit of the methods described herein is that the small molecules under study are not labeled, this is of value in practical applications because of the difficulty of labeling small molecules and the consequent interferences of the labeling groups in binding studies.

All references cited herein are incorporated in their entireties by reference. Further, while exemplary embodiments of the invention have been shown and described, modifications thereof can be made by one skilled in the art without departing from the spirit and teachings of those embodiments. The embodiments described herein are exemplary only, and are not intended to be limiting. Many variations and modifications of the disclosed embodiments are possible and are within the scope of the claimed invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The disclosures of all patents, patent applications, and publications cited herein are hereby incorporated by reference, to the extent that they provide exemplary, procedural or other details supplementary to those set forth herein.

The invention claimed is:

1. A method of quantifying the efficiency of a drug molecule to a receptor by measuring a differential binding force, the method comprising:
   a) conjugating a magnetic particle to a ligand to form a magnetic particle-ligand conjugate;
   b) adding said conjugate to a receptor, wherein said receptor is immobilized on a surface and forming a ligand-receptor complex;
   c) measuring a first magnetization of said complex;
   d) subjecting said complex to a gradually increasing force, wherein said force is increased in increments, and measuring the magnetization at each incremental force value;
   e) determining the dissociation force (F1) of the complex;
   f) reforming the complex;
   g) adding a drug molecule to said complex to form a second complex; or alternatively, adding the drug molecule to the receptor prior to step f, then adding the ligand to form the second complex;
   h) measuring the dissociation force (F2) of said second complex by repeating steps d and e;
   i) subtracting F1 from F2 to quantify the differential binding force of said drug molecule to said ligand-receptor complex.

2. The method of claim 1, wherein in step e, said dissociation of the complex occurs when consecutive magnetization values decrease by a maximum value.

3. The method of claim 1, wherein in said ligand is selected from a group comprising nucleic acids and proteins.

4. The method of claim 1, wherein said receptor is selected from a group comprising nucleic acids and proteins.

5. The method of claim 1, wherein said drug molecule is selected from the group comprising synthetic organic molecules and molecules extracted from natural products.

6. The method of claim 1, wherein said drug molecule is label-free.

7. The method of claim 1, wherein said drug molecule is a racemic mixture.

8. The method of claim 7, wherein said drug molecule is an enantiomer.

9. A method of determining enantiomeric selectivity of a drug for a target; the method comprising:
   a) conjugating a magnetic particle to a ligand to form a magnetic particle-ligand conjugate;
   b) adding said conjugate to a receptor, wherein said receptor is immobilized on a surface and forming a ligand-receptor complex;
   c) measuring a first magnetization of said complex;
   d) subjecting said complex to a gradually increasing force, wherein said force is increased in increments, and measuring the magnetization at each incremental force value;
   e) determining the dissociation force (F1) of the complex;
   f) reforming the complex;

g) adding a first enantiomer to said complex to form a second complex; or alternatively, adding the first enantiomer to the receptor prior to step f, then adding the ligand to form the second complex;

h) measuring the dissociation force (F2) of said second complex by repeating steps d and e;

i) subtracting F1 from F2 to quantify the differential binding force of said first enantiomer to said ligand-receptor complex;

j) adding a second enantiomer to said complex to form a second-enantiomer complex comprising the second enantiomer; or alternatively, adding the second enantiomer to the receptor prior to step f, then adding the ligand to form the second-enantiomer complex comprising the second enantiomer;

k) measuring the dissociation force (F2') of said second-enantiomer complex comprising the second enantiomer by repeating steps d and e;

l) subtracting F1 from F2' to quantify the differential binding force of said second enantiomer to said ligand-receptor complex;

m) subtracting said differential binding force of said second enantiomer from said differential binding force of said first enantiomer; and determining which enantiomer is most tightly bound to said receptor.

10. The method of claim 9, wherein in step e, and step c said dissociation of the complex occurs when consecutive magnetization values decrease by a maximum value.

11. The method of claim 9, wherein in said ligand is selected from a group comprising nucleic acids and proteins.

12. The method of claim 9, wherein said receptor is selected from a group comprising nucleic acids and proteins.

13. The method of claim 9, wherein said drug molecule is selected from the group comprising synthetic organic molecules and molecules extracted from natural products.

14. The method of claim 9, wherein said drug molecule is label-free.

15. A method of determining the selectivity of a nucleic acid sequence for a drug molecule, the method comprising:

a) conjugating a magnetic particle to a ligand to form a magnetic particle-ligand conjugate;

b) adding said conjugate to a first receptor wherein said first receptor comprises a first nucleic acid sequence, and wherein said first receptor is immobilized on a surface and forming a ligand-first-receptor complex;

c) measuring a first magnetization of said ligand-first-receptor complex;

d) subjecting said ligand-first-receptor complex to a gradually increasing force, wherein said force is increased in increments, and measuring the magnetization at each incremental force value;

e) determining the dissociation force (F1) of the ligand-first-receptor complex;

f) reforming the ligand-first-receptor complex;

g) adding a drug molecule to said complex to form a second ligand-first-receptor complex; or alternatively, adding the drug molecule to the receptor prior to step f, then adding the ligand to form the second ligand-first-receptor complex;

h) measuring the dissociation force (F2) of said second complex by repeating steps d and e;

i) subtracting F1 from F2 to quantify the differential binding force of said drug molecule to said ligand-first-receptor complex;

j) adding said conjugate to a second receptor, wherein said second receptor comprises a second nucleic acid sequence that differs from said first receptor by at least one nucleic acid, and wherein said receptor is immobilized on a surface and forming a ligand-second-receptor complex;

k) measuring a first magnetization of said ligand-second-receptor complex;

l) subjecting said ligand-second-receptor complex to a gradually increasing force, wherein said force is increased in increments, and measuring the magnetization at each incremental force value;

m) measuring the dissociation force (F1') of the ligand-second-receptor complex, n) reforming the ligand-second-receptor complex;

o) adding a drug molecule to said ligand-second-receptor complex to form a second ligand-second-receptor complex; or alternatively, adding the drug molecule to the receptor prior to step f, then adding the ligand to form the second ligand-second-receptor complex;

p) measuring the dissociation force (F2') of said second ligand-second-receptor complex by repeating steps d and e;

q) subtracting F1' from F2' to quantify the differential binding force of said drug molecule to said ligand-second-receptor complex;

r) comparing said differential binding force of said drug molecule to said ligand-second-receptor complex and the differential binding force of said drug molecule to said ligand-first-receptor complex; and s) determining from step r the selectivity of said nucleic acid sequence of said receptors for said drug molecule.

16. The method of claim 14, wherein in step e, and step c said dissociation of the complex occurs when consecutive magnetization values decrease by a maximum value.

17. The method of claim 14, wherein in said ligand is selected from a group comprising nucleic acids and proteins.

18. The method of claim 14, wherein said first and second receptors are selected from a group comprising nucleic acids and proteins.

19. The method of claim 14, wherein said drug molecule is selected from the group comprising synthetic organic molecules and molecules extracted from natural products.

20. The method of claim 14, wherein said drug molecule is label-free.

* * * * *